United States Patent

Iwasaki

[11] Patent Number: 4,534,615
[45] Date of Patent: Aug. 13, 1985

[54] SCANNING TYPE LASER SYSTEM
[75] Inventor: Kenji Iwasaki, Utsunomiya, Japan
[73] Assignee: Tokyo Shibaura Denki Kabushiki Kaisha, Japan
[21] Appl. No.: 553,056
[22] Filed: Nov. 18, 1983
[30] Foreign Application Priority Data
Nov. 22, 1982 [JP] Japan ................... 57-203595
[51] Int. Cl.³ .................. G02B 27/08; G02B 27/17
[52] U.S. Cl. ......................... 350/6.1; 350/4.1; 350/6.2
[58] Field of Search .......... 350/6.1, 6.2, 6.5, 4.1

[56] References Cited
U.S. PATENT DOCUMENTS 3,670,260 6/1972 Koester et al. ............ 331/94.5
4,003,626 1/1977 Reinke et al. ............. 350/6
4,212,516 7/1980 Sawamura ............... 350/96.24

OTHER PUBLICATIONS

Grojean et al., "Production of Flat Top Beam Profiles for High Energy Lasers," Review of Scientific Instruments, vol. 51, No. 3, Mar. 1980, pp. 375-376.
Patent Abstracts of Japan, vol. 6, No. 82(P-116) (960), May 20, 1982, and JP-A-57 19712 (Fuji Shashin Koki K.K) Feb. 2, 1982.
Fujii et al., "Fibre Bundle Scanner for Laser Photocoagulation Treatment," Optics and Laser Technology, vol. 14, No. 1, Feb. 1982, pp. 39-40.

Primary Examiner—John K. Corbin
Assistant Examiner—Rebecca D. Gass
Attorney, Agent, or Firm—Finnegan, Henderson, Farabow, Garrett & Dunner

[57] ABSTRACT

A laser system emits a laser beam from a laser oscillator through a kaleidoscope to make intensity distribution of the laser beam uniform. This laser system is a scanning type in which a plurality of kaleidoscopes are bundled together to form a kaleidoscope bundle. The laser beam from the laser oscillator is scanned and is applied to the input ends of the respective kaleidoscopes of the kaleidoscope bundle successively.

15 Claims, 13 Drawing Figures

F I G. 5
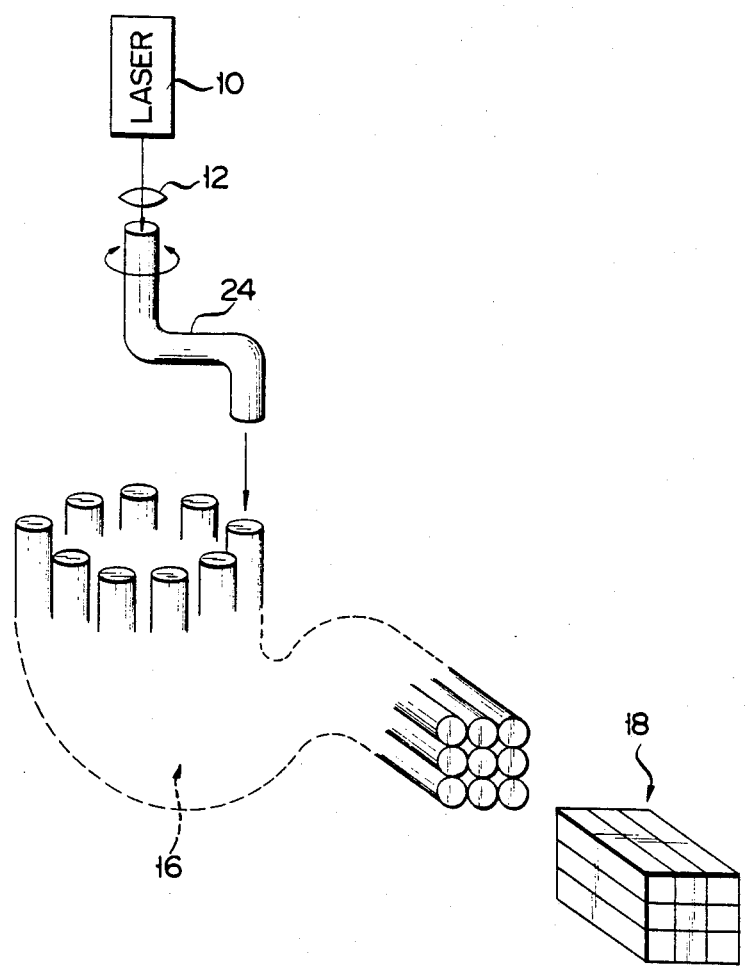

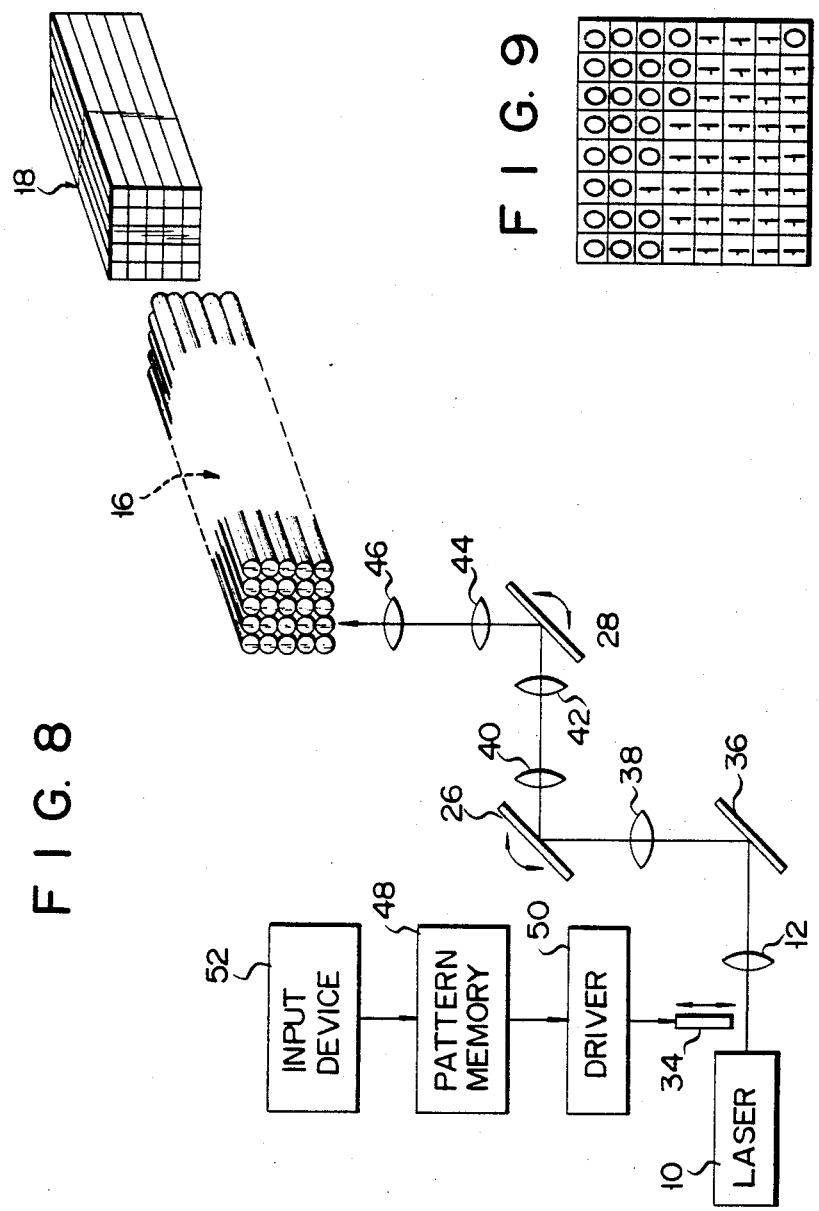

SCANNING TYPE LASER SYSTEM

BACKGROUND OF THE INVENTION

This invention relates to a laser system and, more particularly, to a scanning type laser system which emits a laser beam of uniform intensity distribution for medical treatment purposes.

The use of laser technology in the medical treatment of a variegated lesion such as a birthmark, freckle, or the like on the skin surface of a living body is known. Other methods are also known such as baking using electric drying and hardening, cell deconstruction using dry ice, surgery including cutting and slicing, and skin transplantation. However, all of these methods have disadvantages including a large invasion area, pain, long treatment periods, ineffectiveness and lengthy hospitalizations.

The method of baking the variegated lesion with a laser beam provides the advantage that, since a smaller invasion area is required, there is less pain. However, since the light intensity distribution perpendicular to the advancing direction of a laser beam is generally not uniform, it is difficult to obtain a maximum effect.

Contemporary laser treatments are generally classified into two methods. A first method emits a laser beam directly onto the variegated lesion, and a second method emits the laser beam onto the variegated lesion, after the beam has been passed through a light tramsmitting means such as an optical fiber. In the first method, the laser beam has a convex distribution of light intensity that is strongest at the center and gradually weakens towards the outside of the beam. In the second method, the laser beam emitted from the output end of a fiber has a far field pattern determined by the characteristics of the fiber, and the configuration of the light intensity distribution of the laser beam is complex, therefore it is in possible to obtain a beam of uniform distribution. Both of these methods result in irregular exposure of the laser beam.

To solve such problems, a kaleidoscope of the type, for example, described in an article of Grojean et al. (Review of Scientific Instruments, Vol. 51, No. 3, March, 1980, American Institute of Physics) can be employed. In the kaleidoscope, the light beam propagates while fully reflecting at the peripheral surface of the kaleidoscope, and the light intensity distribution is uniform at the beam emitting end of the kaleidoscope. By using a kaleidoscope which comes into intimate contact with a variegated lesion, the laser beam can be emitted to the variegated lesion with a substantially uniform distribution of light intensity. The configuration of the field wherein the laser beam is irradiated can be appropriately selected by fundling the kaleidoscopes. The laser beam emitted from the kaleidoscope beam emitting end is abruptly spread in the ambience to permit the abrupt decrease of a beam intensity, and the beam loses the coherency. Accordingly, this way of using the kaleidoscope has an advantage in that security is higher, even if the output beam should be mistakenly directed to another portion of the body, such as the eyes.

The kaleidoscope is a light transmitting medium in the form of a transparent square bar made of acrylic meterial or optical glass, or a hollowed square pipe made of metal. In the former kaleidoscope, the light beam is fully reflected at the peripheral surface of the bar by the difference of the reflectances of the bar and ambience. In the latter kaleidoscope, the internal surface is a mirror surface for fully reflecting the light beam, to randomly spread the beam. The both end faces of the kaleidoscope are flat.

Where the kaleidoscope is coupled to the ruby laser for medical treatment purposes, the laser output per unit area is 0.4 Joule/mm$^2$, with specifications wherein the cross-sectional area of the beam emitting end of the kaleidoscope is 10 mm × 10 mm, the output of the ruby laser (of 0.691 μm in wavelength) is 40 Joule, and the pulse width of the pulse oscillating laser is 1 ms. This laser output is enough to destroy the variegated lesion when the lesion is irradiated with the laser beam while bringing the output end of the kaleidoscope into contact with the lesion.

In some cases, use of the argon laser is preferable to use of the ruby laser, since the distinguish length (i.e., the depth wherein 90% of the laser beam is absorbed) of the laser beam for a living organism and the light absorption characteristics of the variegated lensions differ with the types of laser beams. In general, the ruby laser is suitable for treatment of a brown or black variegated lesion and the argon laser is for a red variegated lesion. In this regard, the argon laser is of the continuous output type, with a wave length of about 0.5 μm. In treating the variegated lesion, a laser beam of approximately 4 W is led to the lesion by an optical fiber which is about 1 mm in core diameter. The output end of the argon laser is 1 mm φ and is small, being limited in the following ways. First, since the area of the variegated lesion is generally at least 1 cm φ, to irradiate the entire area of the variegated lesion with the argon laser, the output end of the optical fiber must be displaced on the lesion several times, for a complete irradiation. Secondly, through the irradiation of several steps, it is impossible to uniformly irradiate the entire surface of the lesion, since the configuration of the cross section of the optical fiber is circular.

To obtain uniform irradiation, the use of the kaleidoscope in argon laser irradiation may be considered effective. Actually, however, use of the kaleidoscope increases the cross-sectional area of the laser emitting end, resulting in a reduction of the output density. To be more specific, the argon laser provides a continuous oscillating output of about 4 W. For the optical fiber with an output end of 1 mm φ, the output density of the argon laser is 509 W/cm$^2$. If the kaleidoscope with a light emitting end area of 10 mm × 10 mm is connected to the argon laser, the output density is 4 W/cm$^2$, which value indicates a 0.79% of that in the case of optical fiber use. Such a low output density of 4 W/cm$^2$ would preclude the treatment of the variegated lesion, since in the laser beam treatment, with an instantaneous absorption of an extremely high energy to the variegated lesion, only the variegated lesion is destroyed while normal cells are intact.

For the above reasons, a laser system capable of uniformly irradiating the variegated lesion with a laser beam, at a high output density and over a wide area, is very much in demand. Thus, it is impossible to widen the cross-sectional area of the beam emitting end by connecting the kaleidoscope to the laser system at a low output density, such as the argon laser.

Further, in variegated lesion treatment, it is necessary to irradiate only the lesion with the laser beam, not that portion of the body containing normal cells. Actually, whether or not the cells in the irradiation field are normal or not depends on the judgement of an operator, which inevitabaly entails some uncertainty.

SUMMARY OF THE INVENTION

Accordingly, an object of the invention is to provide a scanning type laser system which can uniformly emit a laser beam at a high output density and over a wide area.

To achieve the above object, there is provided a scanning type laser system comprising a laser oscillator, a kaleidoscope bundle formed of a plurality of kaleidoscopes, and a scanner for scanning the laser beam emitted from the laser oscillator to apply the laser beam into the respective kaleidoscopes successively.

BRIEF DESCRIPTION OF THE DRAWINGS

FIG. 5 is a view illustrating a scheme of a fifth embodiment according to the present invention;

FIG. 8 is a view illustrating a scheme of a eighth embodiment according to the present invention;

FIG. 9 shows an example of data stored in a pattern memory used in the eighth embodiment;

DETAILED DESCRIPTION OF THE PREFERRED EMBODIMENTS

Figure 1:
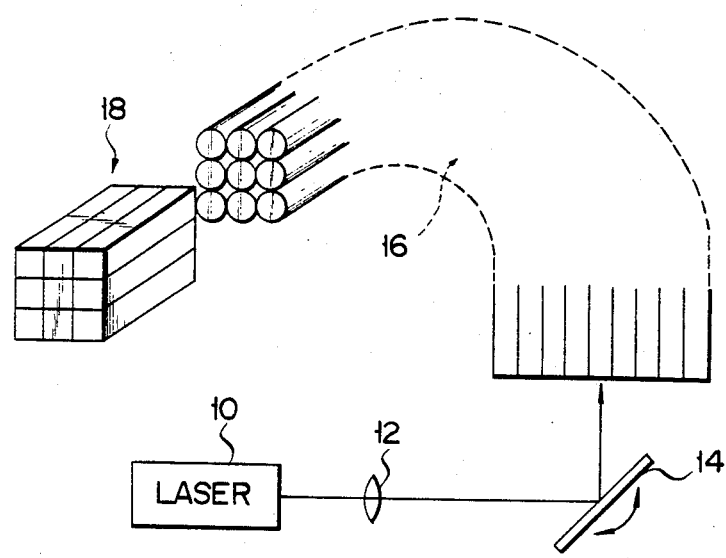
FIG. 1 is a view illustrating a scheme of an embodiment of a scanning type laser system according to the present invention.

An embodiment of a scanning type laser system according to the present invention will be described with reference to the accompanying drawings. FIG. 1 shows a scheme of a first embodiment of the present invention. A laser beam emitted from a laser oscillator 10 is incident on a scanning mirror 14 through a condenser 12. The scanning mirror 14 is rotated in the direction of an arrow by a stepping motor (not shown), so that the laser beam reflected from the scanning mirror 14 is scanned in a sector fashion. The reflected laser beam enters a kaleidoscope bundle 18 via a light guide 16. The light guide 16 is comprised of plurality of optical fibers (nine in this embodiment), each of which is circular in cross section. At the light input end of the light guide 16, i.e., at the end closer to the scanning mirror 14, these optical fibers are arrayed in a line along the scanning direction of the laser beam. At this middle portion, the optical fibers are twisted. At the light emitting end, i.e., at the end closer to the kaleidoscope bundle 18, those optical fibers are arrayed in a 3×3 matrix fasion. In this example, the kaleidoscope bundle 18 consists of nine kaleidoscopes, each having a square cross section, which are bundled in a 3×3 matrix fasion, the bundle itself being rectangularly shaped in cross section. The light guide 16 and the kaleidoscope bundle 18 are so positioned by a holder (not shown) that the optical fibers are respectively coincident with the kaleidoscopes at their centers.

With such an arrangement, the laser beam emitted from the laser oscillator 10 is scanned in a sector fashion by the scanning mirror 14 and successively enters the optical fibers of the light guide 16. If the cross-sectional areas of the optical fibers are equal to one another, the laser beams applied to the respective kaleidoscopes have the same density. Similarly, if the cross-sectional areas of the kaleidoscopes are equal to one another, the laser beams emitted from the output ends of the kaleidoscopes will also be equal to one another with respect to the density. Thus, the distribution of the laser beam intensity at the output end of the kaleidoscope bundle 18 will be uniform. The geometry of the kaleidoscope bundle 18 may appropriately be changed according to the size of the variegated lesion to be treated. If the number of kaleidoscopes is changed, the number of optical fibers making up the light guide 16 will correspondingly be changed. However, even if the number of kaleidoscopes is changed and, hence, the entire cross-sectional area of the kaleidoscope bundle 18 is changed, the output density of the laser beam will not be changed, since the output density is determined by the output power of the laser oscillator 10 and the cross-sectional area of one optical fiber, as previously stated.

As described above, according to the present invention, the laser beam is scanned and successively applied to the respective input ends of the optical fibers arrayed in one-line fasion making up the light guide 16, and is applied to the kaleidoscope bundle 18 through the light guide 16. Since the kaleidoscope bundle 18 consists of a desired number of kaleidoscopes, the variegated lesion can be irradiated uniformly and over a wide area with the laser beam.

Figure 2:
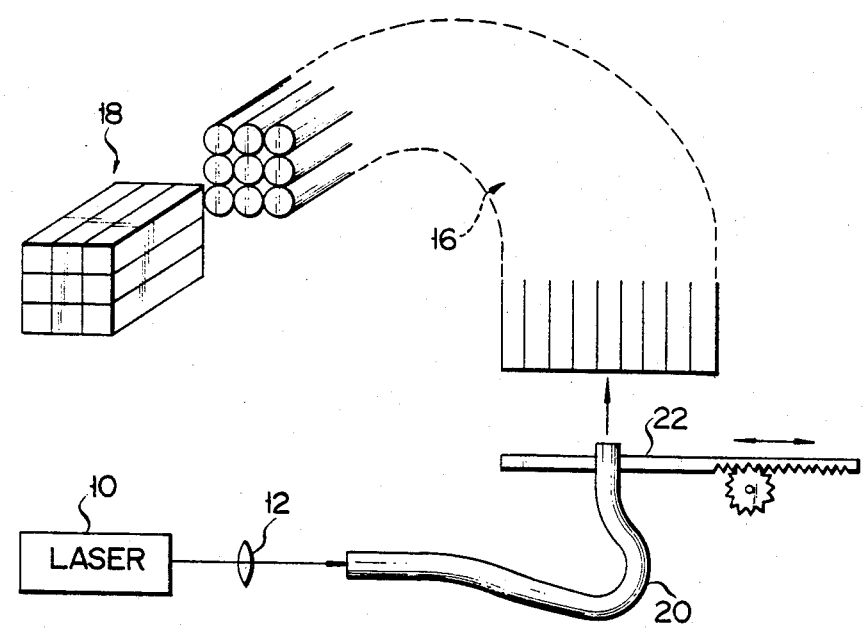
FIG. 2 is a view illustrating a scheme of a second embodiment according to the present invention.
Figure 3:
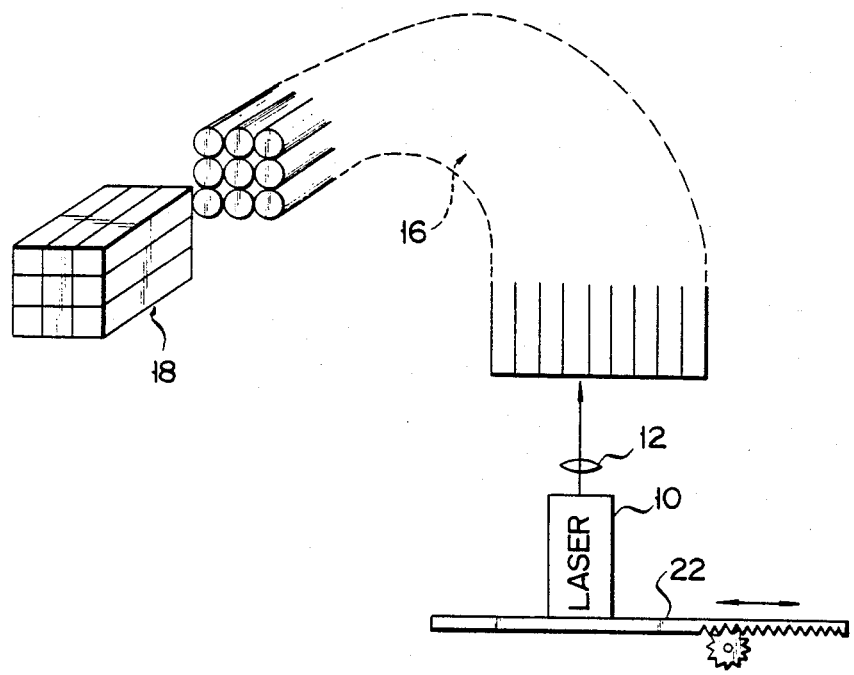
FIG. 3 is a view illustrating a scheme of a third embodiment according to the present invention.
Figure 4:
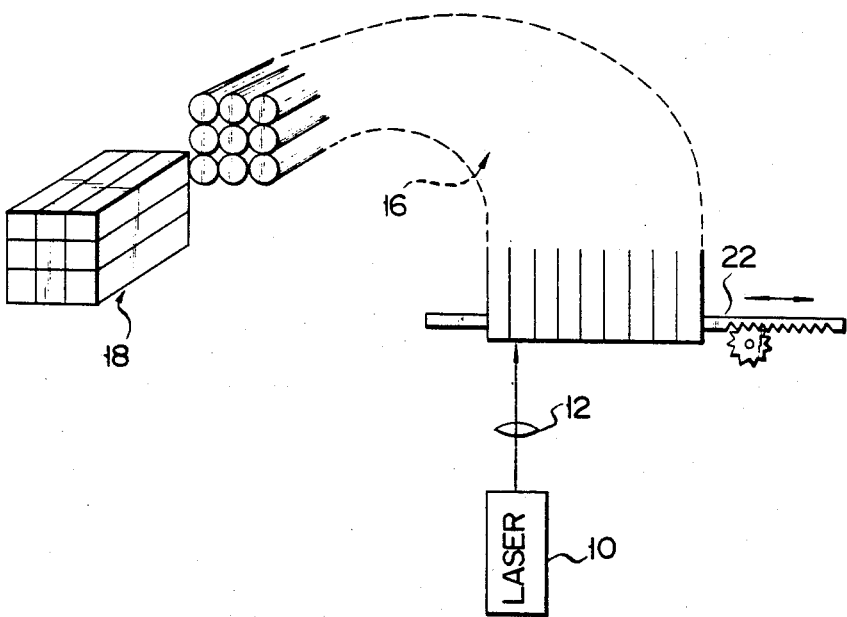
FIG. 4 is a view illustrating a scheme of a fourth embodiment according to the present invention.

Other embodiments of a scanning type laser system according to the present invention will be described. The reference numerals used in the first embodiment will be used for corresponding elements in the other embodiments. FIGS. 2 to 4 illustrate second and fourth embodiments of a scanning type laser system of the present invention. Those embodiments are different from the first embodiment in the configuration of only the scanning mirror 14 as a scanning means. In the second embodiment shown in FIG. 2, the output laser beam from the laser oscillator 10 is guided by a single optical fiber 20 to the light guide 16. The optical fiber 20 is rectilinearly moved by a moving mechanism 22. With the movement of the optical fiber 20, the laser beam emitted from the optical fiber 20 successively enters the respective optical fibers of the light guide 16.

In the third embodiment of FIG. 3, unlike the second embodiment, the laser oscillator 10, per se, is rectilinearly moved by the moving mechanism 22, and the output laser of the laser oscillator 10 directly enters the light guide 16.

In the fourth embodiment shown in FIG. 4, the output laser from the laser oscillator 10 is not scanned, though the light guide 16 at the light input end is linearly moved by the moving mechanism 22. This embodiment successfully attains effects which are similar to those of the previous embodiment.

Figure 6:
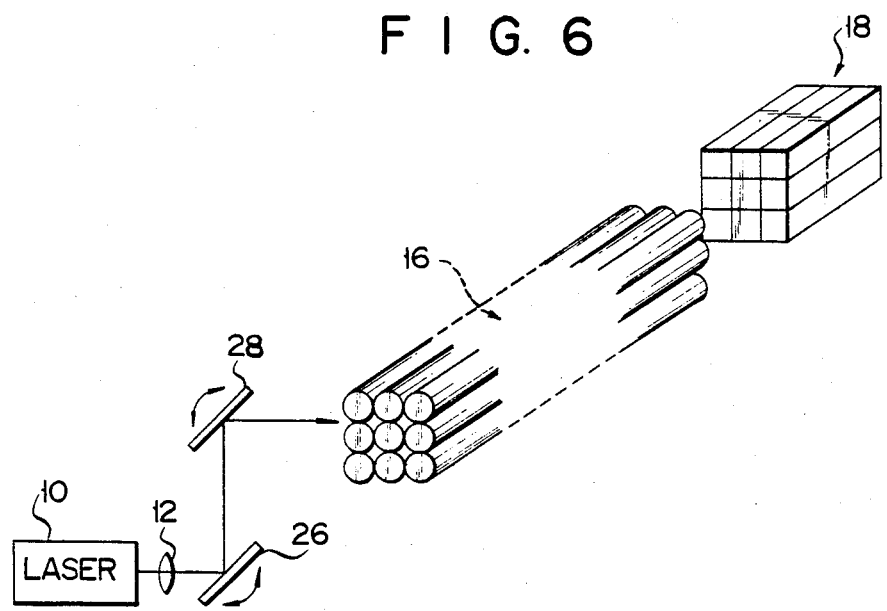
FIG. 6 is a view illustrating a scheme of a sixth embodiment according to the present invention.
Figure 7:
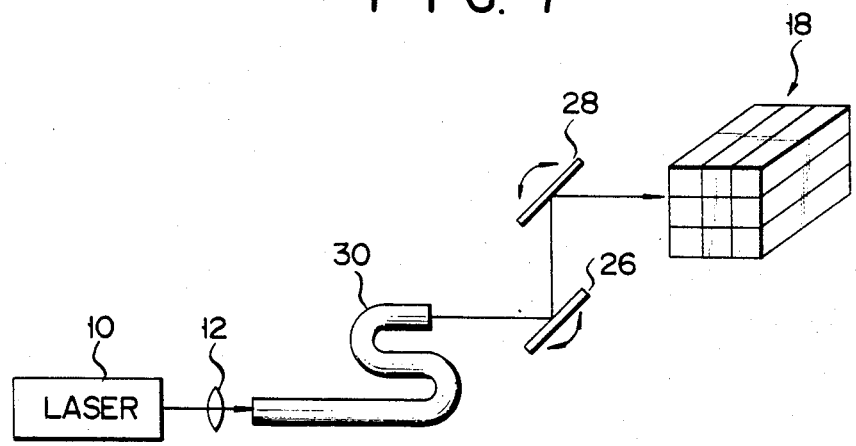
FIG. 7 is a view illustrating a scheme of a seventh embodiment according to the present invention.

In the fifth to seventh embodiments of FIGS. 5 to 7, the structure of the light guide 16 also changes slightly depending on the scanning means. In the fifth embodiment of FIG. 5, a circular scanning, and not a rectilinear scanning, is used for applying the laser beam to the light guide 16. In this embodiment, the optical fibers of the light guide 16 are arrayed circularly, and not rectilinearly at the light input end. The laser oscillator 10 is disposed at the center of the circular array of the optical fibers and the laser beams emitted from the laser oscillator 10 are guided to the periphery of the circular array of the light guide 16, by way of a light guide pipe 24. With the rotation of the light guide pipe 24 in the direction of the arrow, the laser beam successively enters the optical fibers of the light guide 16.

While in the above-mentioned embodiments the laser beam is only scanned one-dimensionally, it may also be scanned two-dimensionally, i.e., in the x and y-directions. In the sixth embodiment of FIG. 6, the output laser beam from the laser oscillator 10 is introduced into the light guide 16 through a scanning mirror 26 for x-direction scanning and another scanning mirror 29 for y-direction scanning. Therefore, the optical fibers making up the light guide 16 are bundled in a 3×3 matrix array over its entire length, having no twisted section at the middle portion. The light guide 16 is for leading the laser beam emitted from the laser oscillator 10 through a flexible member to the kaleidoscope bundle 18, to improve operability. In this respect, a plurality of optical fibers are not necessarily required. In the seventh embodiment of FIG. 7, the laser beam from the laser oscillator 10 is led by means of a light guide 30 consisting of a single optical fiber, and the output laser beam from the light guide 30 successively enters the respective kaleidoscopes in the kaleidoscope bundle 18 through the x-direction scanning mirror 26 and the y-direction scanning mirror 28.

The number and array of the kaleidoscopes may be appropriately selected as required, although in the above-mentioned embodiments the kaleidoscopes are arrayed in a 3×3 matrix fasion.

In the above embodiments, the irradiation field may be properly changed during the manufacturing state, though it cannot be changed later. The laser systems of the above-mentioned embodiments have poor adaptability in terms of their ability to cope with a variety of variegated lesions with different sizes, and may frequently irradiate parts outside the lesion. Embodiments directed toward the elimination of such a defect will be described. An eighth embodiment of a scanning type laser system according to the present invention is illustrated in FIG. 8. The output laser beam from the laser oscillator 10 is incident on a fixed mirror 36 through a shutter 34 and a condenser 12. The shutter 34 interrupts or does not interrupt an optical path by its vertical movement as indicated by the arrow. The optical path of the laser beam is turned 90° by means of the fixing mirror 36 and is transmitted to the light guide 16 through a two-dimensional scanning means including the x-direction scanning mirror 26, the y-direction scanning mirror 28, and condensers 38, 40, 42, 44 and 46. The light guide 16 is composed of optical fibers two dimensionally arrayed like the kaleidoscope bundle 18. The vertical movement of the shutter 34 for interrupting or not interrupting the optical path is done with the assistance of a driver 50 under control of the data derived from a pattern memory 48. The pattern memory 48 has the array of memory cells shown in FIG. 9, which is similar to the array of the kaleidoscope bundle 18, and stores "1" and "0" data in the memory cells according to the interruption/non-interruption of the optical path to the kaleidoscopes. The data is manually written into the pattern memory 48 by use of an input device 52.

According to this embodiment, when the size of a variegated lesion is smaller than the irradiation field of the kaleidoscope bundle 18, it is sufficient to shut off the laser beam entering the kaleidoscopes disposed on the normal portion. More specifically, "1"/"0" data is pre-stored in the pattern memory 48 according to the interruption/non-interruption of the optical path. In synchornism with the x and y-directional scannings of the laser beams, data is read out from the memory 48, and with the reading out of the data, the shutter 34 moves up and down, to interrupt or not interrupt the optical path. Then, the laser beam entering the undesired kaleidoscopes can be shut off, while obtaining a uniform irradiation of the laser beams at a predetermined density for the variegated lesion only.

Figure 10:
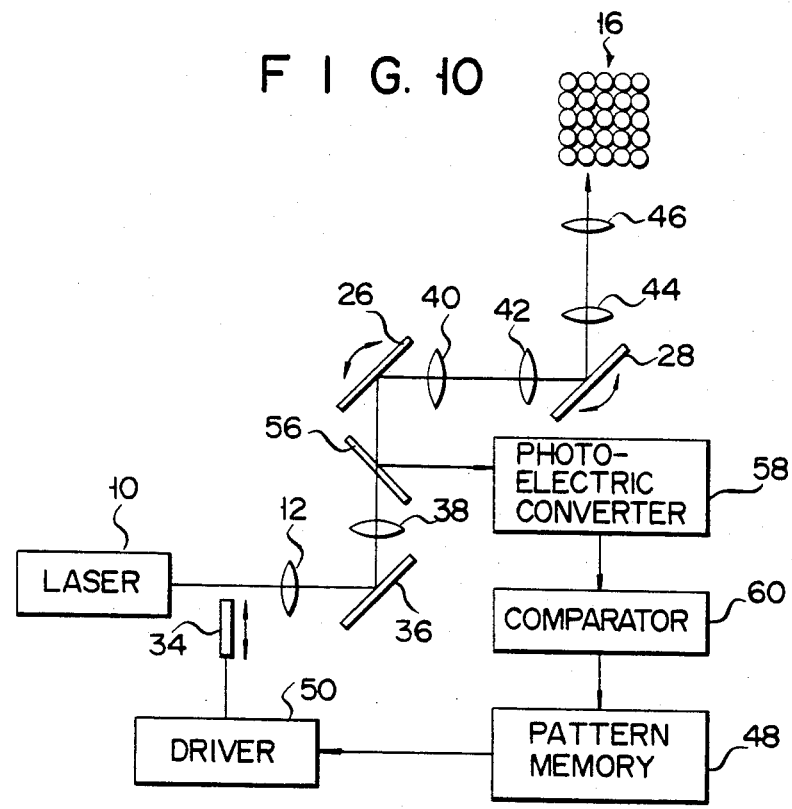
FIG. 10 is a block diagram of a ninth embodiment according to the present invention.

The ninth embodiment shown in FIG. 10 automatically writing the data to the pattern memory. Generally, it is very difficult for an operator to exactly judge whether the cells are variegated or not. The ninth embodiment of FIG. 10 uses the reflectance of the cells for this purpose. To be more specific, a dichroic mirror 56 is provided in the optical path from the laser oscillator 10 to the light guide 16, e.g. between the condenser 38 and the x-directional scanning mirror 26. Generally, a dichroic mirror allows the incident rays of light coming from one of the surfaces to pass therethrough, while effectively reflecting the rays of light incident on the other surface. In this embodiment, the dichroic mirror 56 is so located that it allows the laser beam from the laser oscillator 10 to pass therethrough and reflects the reflecting laser beam which is reflected at an object under irradiation and is led through the same optical path as that of the irradiated laser beam. The laser beam reflected from the object under irradiation and from the dichroic mirror 56 is input to a photo-electric converter 58 where it is converted into a signal corresponding to the intensity of the reflected laser beam. The output signal from the photo-electric converter 58 is compared with a reference value in a comparator 60. Data representing the results of comparison is written into a pattern memory 48. The reference value is in accordance with the output laser beam. The reflectance of the object under irradiation is detected by comparing the reflected laser beam with the reference value.

Figure 11:
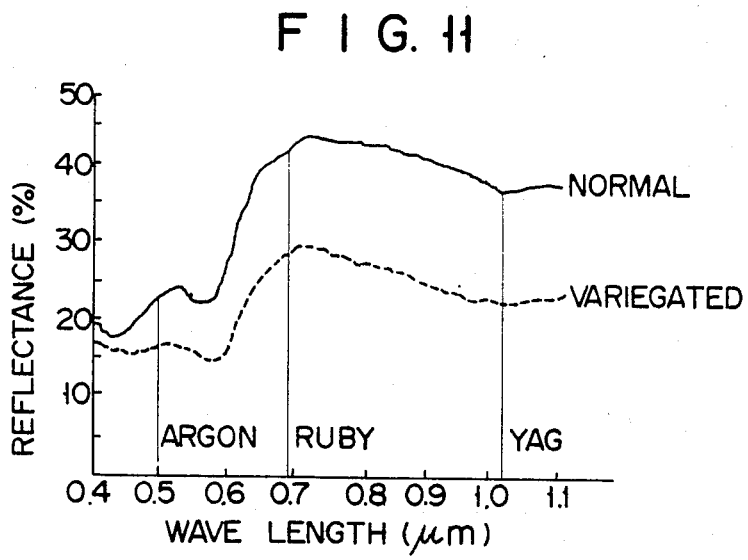
FIG. 11 is a graph illustrating a variation in the reflectance of cells being used in discriminating variegated cells from normal cells, which variation is used in the ninth embodiment.

In treating the variegated lesion by the ninth embodiment, a small laser output, on the order of mW, is first produced by the laser oscillator 10. Then, the x and y-directional scanning mirrors 26 and 28 are rotated to scan the laser beam, and the object under irradiation is irradiated with the laser beam through the kaleidoscopes. The object reflects the laser beam at a reflectance level which depends on the organic state of the laser irradiated portion of the object and the type of laser beam used. An example of this is illustrated in FIG. 11. In the graph of FIG. 11, an abscissa represents a wave length and an ordinate represents a reflectance. The characteristics curve indicated by the solid line represents a reflectance of normal cell, and the characteristic curve indicated by the broken line represents a reflectance of variegated lesion. The reflectance of the variegated lesion is lower than that of the normal cell, as shown. Therefore, if the wave length of the laser beam and the reflectance of the laser irradiated portion are known, it can be checked as to whether the cells in such portion are variegated or not. In this embodiment, since the wave length of the laser beam from the laser oscillator 10 is known, the reflectance is used for the judgement of normal or variegated cells. More specifically, a signal corresponding to the intensity of the reflected laser beam, which signal is produced by the photo-electric converter 58, is compared with the reference value representing a given reflectance. Based on the results of this comparison, it is then known whether the reflectance of the object is above or not the reference value, i.e., whether the cells irradiated are variegated or not. This comparison is made for each of the unit areas of the object which correspond to each kaleidoscope, and the comparison result is stored in the corresponding memory cells of the pattern memory 48. For example, in the case of the argon laser, when the reflectance is 20% or less, the cells with such reflectance are judged to be variegated, and data "0" is stored in the pattern memory 48. Where the reflectance is in excess of 20%, those cells are judged to be normal and data "1" is stored in the memory 48. The data writing operation is completed of a single scanning of the kaleidoscope bundle 18 with the laser beam. Then, the laser output is increased to a desired value, and the laser beam entering the kaleidoscopes is permitted to pass or shut off during the scanning of the laser beam according to the data of the pattern memory 48.

Instead of the above-mentioned comparison method of obtaining the reflectance, an optical filter may be provided on the proceeding stage of the photo-electric converter 58, allowing a laser beam of a predetermined intensity or more to pass therethrough. Alternatively, a half-mirror may be provided on the incident optical path leading to the kaleidoscopes. The incident laser beam guided by the half-mirror would be compared to the reflecting laser beam, to obtain the reflectance. As described above, if the reflectance itself is detected, a careful treatment of the variegated lesion is possible by varying the laser output according to the reflectance.

Figure 12:
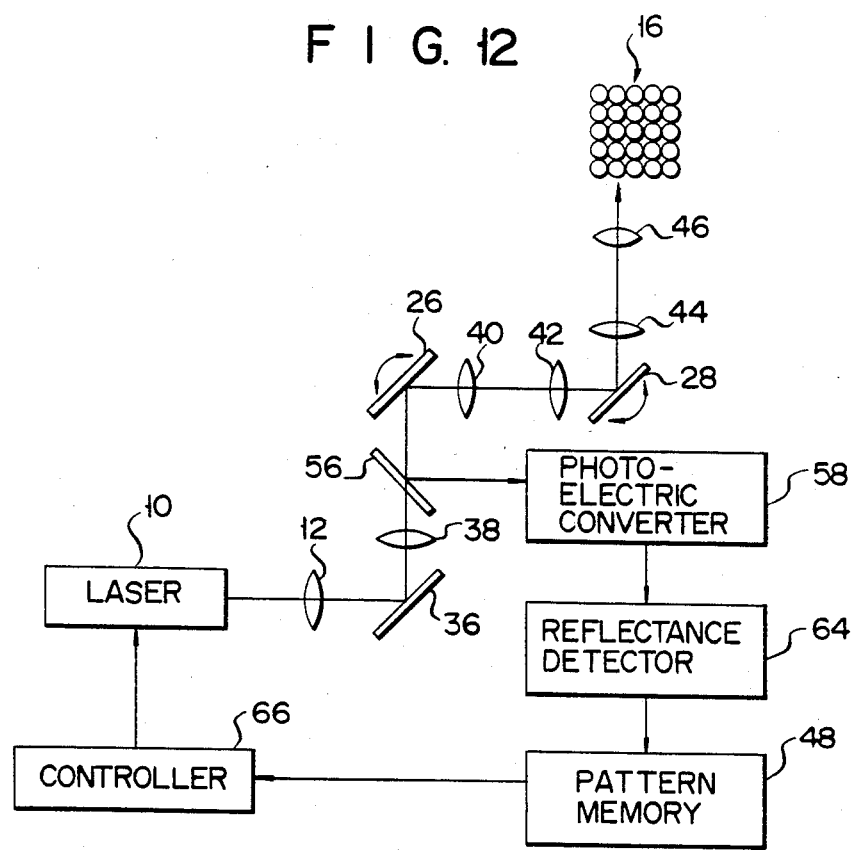
FIG. 12 is a block diagram of a tenth embodiment according to the present invention.

A tenth embodiment varying the laser output will be described with reference to FIG. 12. The output of the photo-electric converter 58 is input to a reflectance detector 64 which in turn writes the reflectance data into the pattern memory 48. In the present embodiment, the optical path of the laser beam is not shutt off for limiting the laser beam applied area to a necessary area, but the output of the laser oscillator 10 is varied. The output of the pattern memory 48 is supplied to a controller 66 for adjusting the output of the laser oscillator 10.

Figure 13:
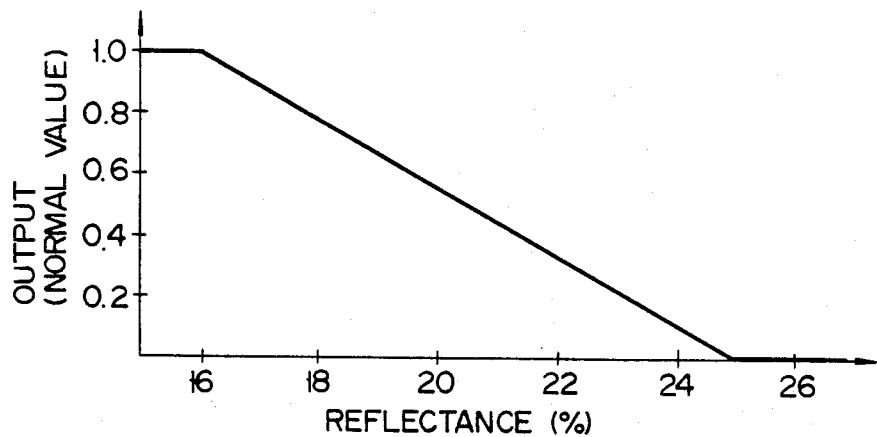
FIG. 13 is a graph illustrating a characteristic of the laser output of the tenth embodiment.

According to this embodiment, the laser output is controlled in the following manner according to the reflectance stored in the pattern memory 48. As described above, since that portion of the object under irradiation which has a low reflectance has variegated cells, the laser output is increased in irradiating such a portion. On the other hand, the laser output must be decreased or zeroed for that portion of the object which has a high reflectance. Toward this end, the controller 66 varies the output of the laser oscillator 10 according to the reflectance read out from the pattern memory 48 as shown in FIG. 13, in synchronism with the scanning of the laser beam. Via the controller 66, the output of the laser oscillator 10 is adjusted to the rated output for below 16% of the reflectance. It is limited to zero for over 25% of the reflectance. For 10 to 25% of the reflectance, the output of the laser oscillator 10 is linearly decreased. As may be seen from the above, this embodiment may also irradiate only the variegated lesion, while not irradiating the normal-cell portion of the object under irradiation, enabling careful treatment according to the size of the variegated lesion.

It should be understood that the present invention may be variously changed and modified within the scope of the present invention.

What is claimed is:

1. A scanning type laser system comprising:
   laser oscillating means;
   a kaleidoscope bundle formed of a plurality of kaleidoscopes for transmitting a laser beam emitted from said laser oscillating means; and
   scanning means for scanning a laser beam emitted from said laser oscillating means to apply the laser beam to the respective kaleidoscopes successively.

2. A scanning type laser system according to claim 1, which further comprises control means for varying the intensity of a laser beam applied to said kaleidoscope bundle.

3. A scanning type laser system according to claim 1 or 2, in which said kaleidoscope bundle has a cross-sectional configuration with a plurality of kaleidoscopes arrayed in a matrix and the laser beam from said laser oscillating means is led to said kaleidoscope bundle through flexible light guide means.

4. A scanning type laser system according to claim 3, in which said scanning means is provided between said light guide means and said laser oscillating means, and said light guide means comprises optical fibers which are equal in number to the kaleidoscopes making up said kaliedoscope bundle and at the light emitting end of said light guide means are arrayed corresponding each of said kaleidsocopes.

5. A scanning type laser system according to claim 4, in which the optical fibers of said light guide means are arrayed in a line at the light input end and said scanning means one-dimensionally scans the laser beam along the light input end of said light guide means.

6. A scanning type laser system according to claim 5, in which said scanning means is a scanning mirror.

7. A scanning type laser system according to claim 5, in which said scanning means comprises a mechanism for moving the light input end of said light guide means in relation to the laser beam.

8. A scanning type laser system according to claim 4, in which said optical fibers of said light guide means are arrayed in a circular fasion at the light input end and said scanning means is provided with rotating means for circularly scanning the laser beam along said circularly arrayed optical fibers.

9. A scanning type laser system according to claim 3, in which said scanning means comprises a couple of scanning mirrors for two-dimensionally scanning the laser beam.

10. A scanning type laser system according to claim 2, in which said control means includes shutter means provided in an optical path ranging from said laser oscillating means to said kaleidoscope bundle.

11. A scanning type laser system according to claim 10, in which said shutter means is controlled by data which is pre-set by an input device.

12. A scanning type laser system according to claim 10, in which said shutter means is controlled by the intensity of the laser beam which is emitted from said kaleidoscope bundle and reflected at an irradiation field.

13. A scanning type laser system according to claim 12, which further comprises means for judging whether the intensity of the laser beam which is emitted from said kaleidoscope bundle and reflected at the irradiation field is above or below a predetermined value, and memory means for storing the output from said judging means for each kaleidoscope, and in which said shutter means shuts off an optical path in synchronism with the laser beam scanning according to the output from said memory means.

14. A scanning type laser system according to claim 2, in which said control means is a controller for varying the output of said laser oscillating means.

15. A scanning type laser system according to claim 14, which further comprises means for detecting the reflectance at the irradiation field corresponding to each kaleidoscope, and memory means for storing the reflectance from said detecting means, and in which said controller controls the intensity of the laser beam in synchronism with the laser beam scanning according to the output from said memory means.

* * * * *